United States Patent [19]

Hummel et al.

[11] Patent Number: 5,264,347
[45] Date of Patent: Nov. 23, 1993

[54] METHOD FOR THE DETERMINATION OF α KETOISOCAPROATE IN BIOLOGICAL SAMPLES USING D-α-HYDROXYISOCAPROIC DEHYDROGENASE FROM LACTOBACILLUS CASEI

[75] Inventors: Werner Hummel, Titz; Udo Wendel, Hilden; Peter Schadewaldt, Duesseldorf, all of Fed. Rep. of Germany

[73] Assignee: Kernforschungsanlage Juelich GmbH, Juelich, Fed. Rep. of Germany

[21] Appl. No.: 924,569

[22] Filed: Aug. 5, 1992

Related U.S. Application Data

[63] Continuation of Ser. No. 407,941, Sep. 15, 1989, abandoned.

[30] Foreign Application Priority Data

Sep. 16, 1988 [DE] Fed. Rep. of Germany ....... 3831450

[51] Int. Cl.$^5$ ............................................. C12Q 1/32
[52] U.S. Cl. ........................................ 435/26; 435/856
[58] Field of Search ............................................. 435/26

[56] References Cited

FOREIGN PATENT DOCUMENTS 0130288 9/1985 European Pat. Off. .

OTHER PUBLICATIONS

Schadewaldt et al., Clinica Chimica Acta 183:171-182 (89).
Hummel et al., Appl. Microbiol. Biotechnol. 21:7-15 (85).
Goodwin et al., Anal. Biochem. 162:536-539 (87).
Bergmeyer ed., "Methods in Enzymatic Analysis" VIII:323-29 (85).
Yamazaki et al., CA 109(23):209686s (1988).
Kallwass et al., CA 112(23):212816(b) (1988).
Qureshi; "High Performance Liquid Chromatographic Methods with Fluorescence Detection for the Determination of Branched-Chain Amino Acids . . . ;" Journal of Chromatography (1987); 400:91-99.
Livesey, et al.; Enzymic Determination of Branched-Chain Amino Acids and 2-Oxoacids in Rat Tissues; Biochem. J. (1980); 188: 705-713.
Bergmeyer (ed.); Methods in Enzymatic Analysis; vol. VIII, pp. 318-329; Verlag Chemie, Weihneim (1985).
Goodwin, et al.; Enzymatic Determination of the Branched-Chain a-Keto Acids; Analytical Biochemistry (1987); 162: 536-539.
Bender; Amino Acid Metabolism, Second Edition; Ch. 8, pp. 175-187.
White, et al.; Principles of Biochemistry, Sixth Edition.
Selma E. Snyderman, et al.; The Relationship between the Branched Chain Amino Acids and Their α-Ketoacids in Maple Syrup Urine Disease; Pediatric Research vol. 18, No. 9, (1984); pp. 851-853.

Primary Examiner—David M. Naff
Assistant Examiner—Sandra Saucier
Attorney, Agent, or Firm—Foley & Lardner

[57] ABSTRACT

The selective determination of α-ketoisocaproate in samples of body fluids, especially in serum, is achieved, without previous separation, directly in the fluid and in the presence of NADH, by means of a KIC-specific D-α-hydroxy-isocaproic dehydrogenase that originates specifically from strains of *Lactobacillus casei* producing this enzyme, in particular strains of *Lactobacillus casei* subspecies *pseudoplantarum* or *casei*. The KIC determination is used, in particular, for diagnosing maple syrup urine disease. Expedient for this purpose are analytical kits which have a divisible stock of D-α-hydroxyisocaproic dehydrogenase from *Lactobacillus casei*, in particular from the *Lactobacillus casei* (DSM 20008).

6 Claims, 2 Drawing Sheets

HicDH aus L.casei

METHOD FOR THE DETERMINATION OF α KETOISOCAPROATE IN BIOLOGICAL SAMPLES USING D-α-HYDROXYISOCAPROIC DEHYDROGENASE FROM LACTOBACILLUS CASEI

This application is a continuation of application Ser. No. 07/407,941, filed Sep. 15, 1989 now abandoned.

BACKGROUND OF THE INVENTION

The present invention relates to a method for selective determination of the α-ketoisocaproate content in samples of body fluids, especially serum samples, by enzymatic reaction in the presence of coenzyme, and to an analytical kit for such a determination.

Ketoisocaproate (KIC) is a metabolite which is generated, normally as an intermediate, in the catabolism of leucine to acetyl CoA and acetoacetate. The relevant portion of the pathway in question is shown below, along with the corresponding portions of the catabolic pathways for two other branched-chain amino acids, isoleucine and valine:

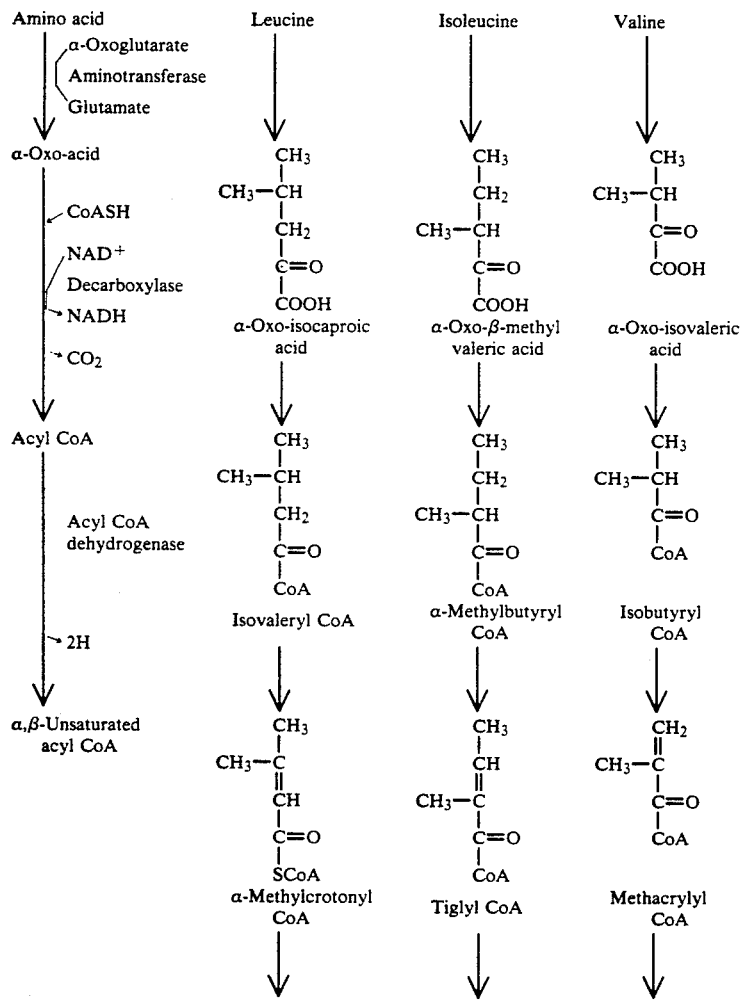

A hereditary anomaly in neonates, called maple syrup urine disease (leucinosis) because of the characteristic odor of the urine, results in a blockage in the breakdown of KIC, as well as of the two other branched-chain keto acids formed, respectively, from valine and isoleucine, due to a failure of normal oxidative decarboxylation. The genetic defect thus affects the branched-chain ketoacid dehydrogenase, resulting in the accumulation of KIC and the other branched-chain keto acids in the serum and, subsequently, in the urine. KIC has a toxic effect on the brain and can, when present in high concentration, result in death of children in infancy or in impaired brain development.

The only successful therapy known for maple syrup urine disease involves adherence to a special diet, in which the intake of leucine, valine and isoleucine in the food is distinctly restricted compared with normal. Frequent checks of the plasma leucine or KIC levels are necessary to monitor the therapy. A peculiarity of this disease is that when there are febrile infections, as occur very often in infancy, there is likewise an increase in leucine and KIC in the blood, which is frequently dangerous. The essential prerequisite for effective therapy is, therefore, a good method of amino acid analysis or KIC analysis. Particularly suitable for bedside monitoring of the patient's metabolism is determination of KIC in urine. A good KIC analysis is an absolute prerequisite for this.

In other metabolic abnormalities and, particularly, in the context of diabetes and liver damage, there may likewise be a dangerous accumulation of physiologically unacceptable levels of KIC, so that selective determination thereof is of considerable importance.

The problem associated with KIC analysis is that both the serum and the urine also contain relatively high concentrations of the two other branched-chain keto acids (ketomethylvalerate=KMV; ketoisovalerate=KIV), which are chemically very similar to KIC and interfere with the KIC determination. Accordingly, there is an extensive literature (twenty-eight publications over the last ten years) dealing with chromatographic separation of these keto acids, after appropriate derivatization, by gas chromatography or high performance liquid chromatography (HPLC). See, for example, J. Chromat. 400 (1987) 91-99. These chromatographic methods are sensitive and reliable but require elaborate apparatus and are rather time-consuming. For this reason, KIC analyses have heretofore been carried out only in specially equipped analytical laboratories.

Although it is known that branched-chain 2-keto carboxylic acids can be analyzed reliably, rapidly and with little effort by enzymatic conversion, to date only the total concentration of the three said keto acids has been measured. See G. Livesey and P. Lund in Biochem. J. 188 (1980) 705-713, particularly at page 711; METHODS IN ENZYMATIC ANALYSIS (Bergmeyer, H. K., ed.) Vol. VIII pages 318-329, especially page 324, Verlag Chemie, Weihneim 1985; and Anal. Biochem. 162 (1987) 536-539.

SUMMARY OF THE INVENTION

It is therefore an object of the present invention to provide a method for the differential determination of KIC in biological samples, which method is readily carried out and yields, without previous separation, sufficiently accurate values selectively for KIC concentration despite the simultaneous presence of KMV and KIV.

It is also an object of the present invention to provide an analytical kit that can be used, without the need for special equipment, for the selective determination of KIC levels in samples prepared from biological fluids.

In accomplishing the foregoing objects, there has been provided, in accordance with one aspect of the present invention, a method for the selective determination of α-ketoisocaproate content in a sample, comprising the steps of (A) providing a sample prepared from a bodily fluid of a subject; (B) bringing the sample, in the presence of NADH, into contact with a *Lactobacillus casei* D-α-hydroxyisocaproic dehydrogenase enzyme that selectively catalyzes conversion of α-ketoisocaproate to α-hydroxyisocaproate; and then (C) measuring the sample for occurrence of the conversion. In a preferred embodiment, the enzyme used in step (B) is isolated from *Lactobacillus casei* subspecies *pseudoplantarum* or *casei*.

In accordance with another aspect of the present invention, an analysis kit is provided that comprises a standardized stock of D-α-hydroxyisocaproic dehydrogenase enzyme and predetermined stock amounts, respectively, of NADH and a buffer compatible with both the enzyme and NADH. In a preferred embodiment, the kit further comprises means for delivering aliquots of at least one of the enzyme, NADH and buffer to a liquid sample.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The method of the present invention entails carrying out a KIC determination, directly in the sample fluid, by means of a KIC-specific D-α-hydroxy-isocaproic hydrogenase from strains of *Lactobacillus casei*, in the presence of NADH, producing α-hydroxyisocaproate and $NAD^+$. Detecting the occurrence of the enzyme-catalyzed reaction, the rate of which can serve as a measure of KIC concentration in the tested sample, can be accomplished by measuring the depletion of NADH cofactor, for example, by monitoring the change in sample absorption (extinction) at 340 nm. Alternatively, the generation of $NAD^+$ can be coupled to a second reaction in situ that consumes $NAD^+$ at a comparable rate and generates a species which is colored or otherwise detectable. Detecting the appearance of the α-hydroxyisocaproate per se may also be feasible.

Since removal of protein is commonly a part of the preparation of serum for general diagnostic testing, it is often convenient to obtain samples for use in the present invention from protein-free sera material. As described in greater detail below, moreover, removal of most or all foreign protein from a sample may be desirable, since potentially interfering enzymes and metabolites are thereby eliminated. Deproteinization of samples is optional, however, in the context of the present invention.

Figure 1:
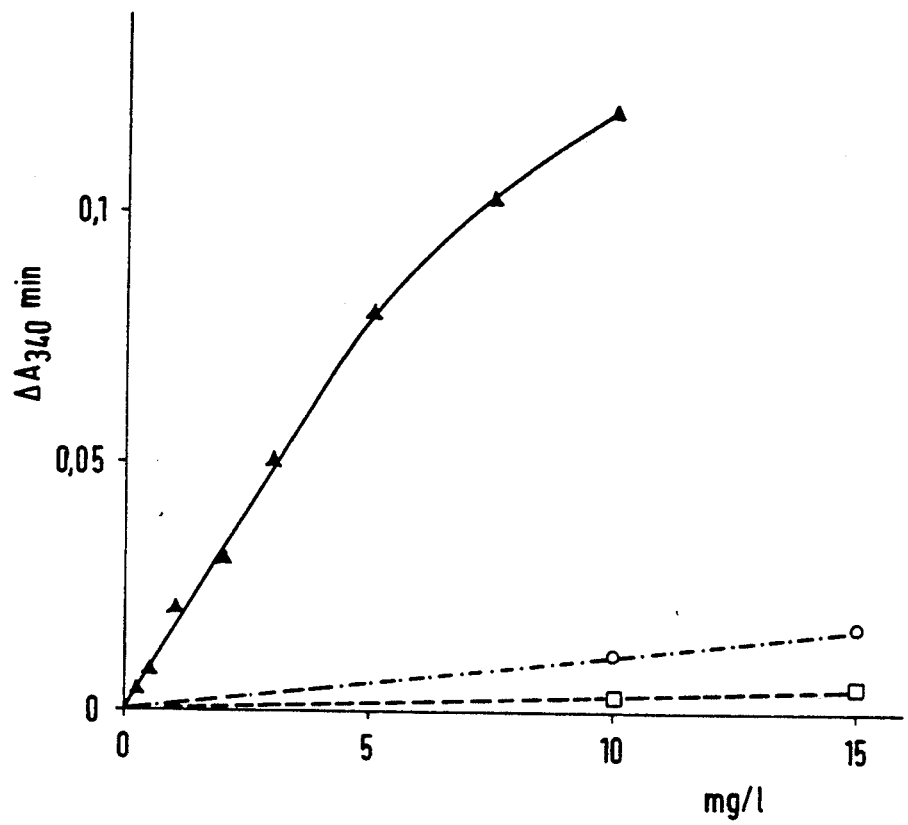
FIG. 1 is a graph depicting kinetics data which illustrate the selectivity of a *Lactobacillus casei* D-α-hydroxyisocaproic dehydrogenase for KIC.

The enzymatic conversion of KIC to the corresponding isocaproate with a KIC-specific α-hydroxyisocaproic dehydrogenase isolated from *Lactobacillus casei*, according to the present invention, surprisingly takes place very much more rapidly than does the parallel conversion of KMV and KIV. This selectivity is illustrated in FIG. 1, which plots a measure of reaction rate (change per minute in absorption at 340 nm), in the presence of NADH and a *Lactobacillus casei* D-α-hydroxyisocaproic dehydrogenase, versus keto-acid concentration for KIC, KMV and KIV, respectively. In FIG. 1, ▲—▲ represents ketoisocaproate, O----O represents ketomethylvalerate and □----□ represents ketoisovalerate, respectively. It can be seen from FIG. 1 that the enzymatic conversions of KMV and KIV can be ignored, at least in a first approximation, relative to the conversion of KIC.

Figure 2:
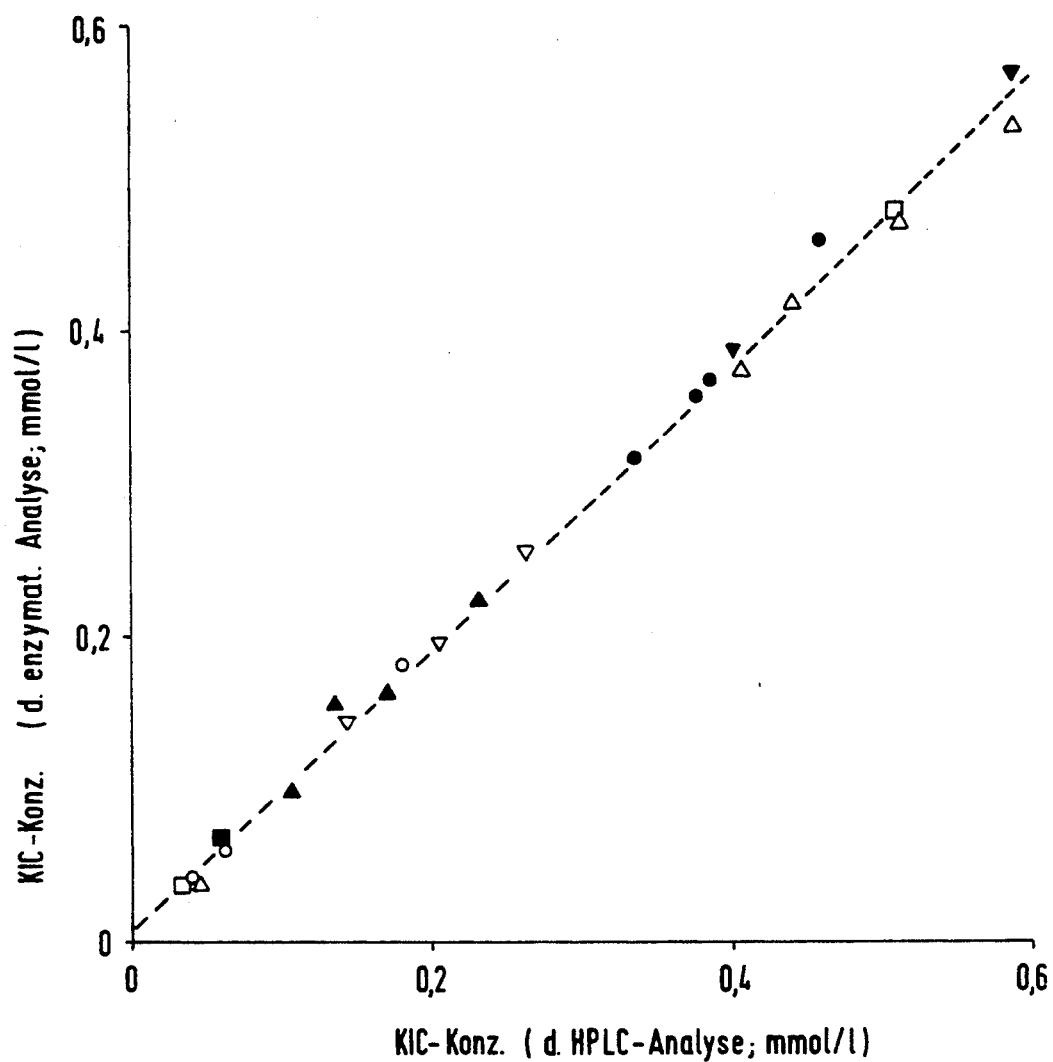
FIG. 2 is a graph showing a comparison of KIC-analytical values determined in accordance with the present invention with corresponding values measured via HPLC.

The present invention provides a convenient and rapid method for monitoring KIC values in organic samples, especially body fluids such as blood or urine. FIG. 2 shows, by comparison with a parallel HPLC determination of KIC values, a check on the analytical accuracy and precision of a method within the present invention. The comparison involved determinations, in a clinical context, of KIC concentrations in the blood of patients with maple syrup urine disease. It is evident from FIG. 2 that the measured points lie almost ideally on a 45° line; thus, the very much more straightforward enzymatic determination pursuant to the present invention is not inferior to HPLC analysis.

A KIC-specific dehydrogenase suitable for use in the present invention is obtained from strains of *Lactobacillus casei* that produce an enzyme with the prerequisite specificity, as described above. This property is readily identified by a relatively straightforward assay; that is, the cultivated strain is disrupted, and the cell-free supernatant obtained by centrifugation is used for the enzyme assay.

Among available strains or subspecies (ssp.), specifically identified as suitable in this manner were *Lactobacillus casei* ssp. *pseudoplantarum* and *casei* (see below). Preferably used in a method according to the present invention is D-α-hydroxyisocaproic dehydrogenase (D-HicDH) isolated from *Lactobacillus casei* ssp. *pseudoplantarum*. in particular the strain deposited on Oct. 25, 1988 under accession number DSM 20008 at the Deutsche Sammlung von Mikroorganismen (Gottingen, FRG).

It is preferred that the activity of KIC-specific enzyme employed in the present invention should be greater than 5 U/mg, which can be achieved, in particular, by a combined purification by phase partition and diafiltration, such that low molecular weight constituents are removed. At least 90% of foreign protein is removed in this way and, hence, potentially interfering enzymes and metabolites are eliminated.

One method for obtaining a suitable a-hydroxyisocaproic dehydrogenase is described in European patent application No. 0 130 288, wherein details about obtaining and purifying this group of enzymes from various microorganisms are given. According to the present invention, however, only enzyme isolated from *Lactobacillus casei* is used, resulting in a surprisingly straightforward determination of KIC in body fluid without special previous separation and without the occurrence of interference, especially by the keto acids related to KIC. Such a considerable improvement in the diagnosis of maple syrup urine disease and other conditions marked by elevated KIC values could not have been deduced from the teachings of the aforementioned European application.

According to EP 130,288, the microorganism is cultivated and the enzyme isolated and purified as follows:

1. Cultivation of the microorganism

For cultivation, *Lactobacillus casei* ssp. *pseudoplantarum* (DSM 20008) is grown in the following medium:

| Glucose | 20 g | |
|---|---|---|
| Yeast extract | 10 g | |
| Meat extract | 0.5 g | |
| Sodium acetate | 5 g | |
| K$_2$HPO$_4$ | 2 g | Complex Medium |
| MgSO$_4$ | 0.2 g | |
| MnSO$_4$ | 0.05 g | |
| Deionized water to make 1 liter. | | |

The pH of this solution is adjusted to 6.5; then it is sterilized for 15 minutes at 121° C. (2 bar). For cultivation, 5 ml of medium in the reagent glass was inoculated with a loop full of *Lactobacillus casei* ssp. *pseudoplantarum* from the agar tube and cultivated for 16 to 20 hours at 30° C. 4 ml of the mature culture was then used as an inoculant culture for 200 ml of medium (in 500-ml Erlenmeyer flasks). 20 to 24 hours later this 200 ml of medium can be used as pre-culture for a 10-liter fermenter, and then 200 liters and 5,000 liters can be inoculated, if desired. The pH, which decreases as growth progresses, is kept at 5.0 in the fermenters with concentrated ammonia. The cultivation in the fermenter is performed with gentle stirring while flooding with nitrogen. Toward the end of the logarithmic growth phase the culture is cooled and the cells harvested by centrifuging. 45 kg of centrifuges cell mass is obtained from 4500 liters of culture. The biomass can be set aside at −20° C. for several months without any great loss of activity.

2. Isolation and purification of the enzyme a) Crude extract 500 g of *Lactobacillus casei* ssp. *pseudoplantarum* (DSM 20008) is suspended in 50 mM of phosphate buffer for pH 7.0, which contains 0.1% (v/v) of 2-mercaptoethanol. The end volume of 1250 ml corresponds to a 40% cell suspension. The cells are disintegrated either in a continuously running glass bead ball mill or in a high-pressure homogenizer. The glass bead ball mill used here is the Model KDL Dynamühle made by Bachofen.

The grinding barrel of a capacity of 600 ml is filled with glass beads measuring 0.25 to 0.5 mm, so that a shaker volume of 510 ml results (85%). The disintegration is performed at a stirring shaft speed of 3000 rpm and a rate of flow of 5 l/h. The cooling jacket of the barrel as well as the bearings of the stirring shaft are cooled while running with ethylene glycol solution at −20° C. in order to prevent the product from heating, insofar as possible. After three passes through the barrel a degree of disintegration of >90% is reached. The pH of the suspension decreases to 6.1 during the homogenization and is restored to pH 7.0 with caustic potash solution. The high-pressure homogenizer can be, for example, the Manton Gaulin Model 15 M-8TA machine (A. P. V. Schröder GmbH, Lübeck). The cell suspension is disintegrated at 550 bar using a special homogenization valve for the disintegration of microorganisms and for a throughput of 54 l/h. After two passes a disintegration of >90% is reached. After each run the homogenate is cooled with a flow-through cooler to temperatures below +10° C. so as to avoid heating the product over 20° C. The pH of the suspension is adjusted after disintegration to pH 7.0.

b) Liquid-liquid distribution

The first distribution is intended to separate the cell fragments from the crude extract in accordance with German Pat. 26 39 129. For this purpose an aqueous two-phase system is prepared, which contains 20% (w/w) of polyethylene glycol 1500, 8% (w/w) phosphate buffer for pH 7.0 and 1250 ml of crude extract in a 2.5 kg system. To achieve the equilibrium of the distribution the two-phase system is stirred for one hour and then separated by centrifuging. Larger volumes are best separated continuously with a plate separate, e.g., such as the Gyrotester B of α-Laval or Westfalia, Model SAOH-205. The upper phase (1440 ml) contains virtually all of the activity (yield 99%) of the D-2-hydroxy-4-methylpentanicaciddehydrogenase. The lower phase contains cell fragments and is discarded. The enzyme-containing upper phase is treated with 2% (w/v) of polyethylene glycol 10,000, 8% phosphate buffer of pH 6.0, and 0.4M of sodium chloride, reckoned on an end volume of 2880 ml, and stirred for one hour. The polyethylene glycol/salt system that forms is allowed to settle in a vertical cylinder; the separation is complete after about one hour. In this separating step, the D-2-hydroxy-4-methylpentanicaciddehydrogenase is extracted into the salty underphase. The separation of the phases is performed after draining out the underphase.

c) Diafiltration

The underphase is concentrated with an Amicon hollow fiber cartridge (Mod. HIP10) and diafiltered by the addition of phosphate buffer for pH 7.0 to a salt concentration of 50 mM.

d) DEAE-Cellulose Chromatography

The concentrated and diafiltered enzyme is pumped onto a 5×30 cm column that is packed with Whatman Cellulose DE 52. The DEAE-cellulose was balanced against a buffer containing 50 mM of phosphate buffer for pH 7.0 and 0.1% (v/v) of 2-mercaptoethanol. The column is first rewashed with about 2 liters of starting buffer and the enzyme is then eluted with a linear gradient (2×1 liters) from 0 to 0.25M of sodium chloride in starting buffer. The D-2-hydroxy-4-methylpentanicaciddehydrogenase elutes with about 0.1M of sodium chloride. The active fractions are concentrated by ultrafiltration and preserved at 4° C. The purification steps are listed in Table 2.

TABLE 2

Purification of D-2-hydroxy-4-methylpentanicacid deydrogenase

| Cleaning step | Volume in ml | Protein in mg | Total activity U | Specific activity U/mg | Yield % | Concentration |
|---|---|---|---|---|---|---|
| Crude extract | 1250 | 30,500 | 18,625 | 0.61 | 100 | 1 × |
| Upper phase I | 1440 | 6,120 | 18,438 | 3.01 | 99 | 4.9 × |
| Lower phase II | 1060 | 3,795 | 15,857 | 4.18 | 85 | 6.9 × |
| Diafiltration | 187 | 3,150 | 15,064 | 4.78 | 81 | 7.8 × |
| DEAE-Cellulose | 493 | 424 | 10,545 | 24.87 | 57 | 40.8 × |

The enzyme preparation obtained after the last step can be used for technical purposes. By additional chromatographic methods, e.g., ion exchange chromatography on Amberlite CG501, gel filtration on Sephacryl S 200 or hydrophobic chromatography on phenyl-Sepharose CL-4B, the enzyme can be further purified up to a specific activity of 110 U/mg. The substrate spectrum is not changed thereby. The molecular weight of the D-2-hydroxy-4-methylpentanicacid-dehydrogenase was determined by gel filtration on Sephacryl S 200 superfine to 73,000±10,000 Dalton by the method of Andrews (Meth. Biochemical Analysis, 18:1-53, (1970)). Dextran blue, ferritin, aldolase, bovine serum albumin, sheep albumin, Chymotrypsinogen A and Cytochrome C were used as calibrating substances.

The present invention is further described below by reference to the following illustrative examples.

EXAMPLE 1

Selection of a suitable enzyme

The species *Lactobacillus casei* is currently divided into five subgroups (subspecies). For purposes of selecting a KIC-selective enzyme, the type strain for each subgroup was tested to find whether the corresponding hydroxy-acid dehydrogenase possessed sufficient selectivity for KIC. The three keto acids KIC, KMV and KIV were used in a concentration of 0.15 mM (final concentration in the assay). An enzyme were deemed suitable if it showed, at this keto acid concentration, a good reaction with KIC and a weak reaction or no reaction at all with KMV and KIV.

For the assay mixture, the microorganisms which had been cultured under customary conditions were harvested, the cells were disrupted by mechanical action, and the supernatant obtained by centrifugation was used as "enzyme solution" for the assay.

Besides the various *Lactobacillus casei* strains, other Lactobacillus strains were also investigated; two typical representatives are listed in a table below.

The assay mixture contained:
0.1M potassium phosphate buffer, pH 7.0;
0.2 mM NADH;
0.020 ml of enzyme solution (0.1–0.2 mg of protein);
0.15 mM keto acid (as shown in the table).

The initial reaction rate was determined by measuring the absorption at 340 nm as a function of time. (The reaction rate is reported in international units (IU)/min.) The results obtained are summarized below.

TABLE 1

Suitability of various Lactobacillus strains for the selective enzymatic determination of KIC.

| Organism | DSM No. | KIC | KMV | KIV |
|---|---|---|---|---|
| *L. casei* ssp. *pseudoplantarum* | 20 008 | 1.37 | 0.12 | 0 |
| *L. casei* ssp. *pseudoplantarum* | 20 207 | 2.00 | 0 | 0.14 |
| *L. casei* ssp. *casei* | 20 011 | 1.07 | 0 | 0.08 |
| *L. case* ssp. *alactosus* | 20 020 | 0.01 | 0 | 0 |
| *L. casei* ssp. *rhamosus* | 20 021 | 0 | 0 | 0 |
| *L. casei* ssp. *tolerans* | 20 258 | 0 | 0 | 0 |
| *L. curvatus* | 20 019 | 1.45 | 1.40 | 0.62 |
| *L. confusus* | 20 196 | 0.64 | 0.90 | 0.11 |

From the table it is evident that enzyme from strains of *Lactobacillus casei* ssp. *pseudoplantarum* and *Lactobacillus casei* ssp. *casei* was suitable for the selective determination of KIC. Conversely, suitable enzyme was not produced by the other subgroups of *Lactobacillus casei* strains investigated. Other Lactobacillus strains similarly investigated which were not of the subspecies *pseudoplantarum* or *casei* were found not to produce enzyme usable for an analytical method within the present invention.

EXAMPLE 2

Enzymatic Selectivity for KIC

To demonstrate the selectivity of a KIC determination according to the invention, a comparative concentration determination of the three keto acids KIC, KMV and KIV was carried out, using D-α-hydroxyisocaproic dehydrogenase from *Lactobacillus casei* ssp. *pseudoplantarum* (DSM 20008). This entailed use of standard solutions of the three keto acids, each of known concentration (0.2 to 15 ωg/ml of assay mixture).

The assay mixture contained:
0.1M potassium phosphate buffer, pH 7.0;
0.2 mM NADH;
0.1 unit of D-HicDH;
stepped concentrations of keto acids.

The initial reaction rates ($\Delta A_{340}$/min) were measured at 340 nm. When these rate values were plotted against the initial concentration of keto acid, the detection sensitivity for KIC was found to be more than ten times better than for KMV and KIV (see FIG. 1). This difference would be sufficient for a selective determination of KIC, for example, in serum.

EXAMPLE 3

Measurement of KIC concentrations in blood plasma

The KIC content in the plasma of healthy subjects and of patients with maple syrup urine disease was determined enzymatically, using a KIC-selective HicDH in accordance with the present invention, and compared with KIC values measured using a chromatographic method. For this purpose, plasma samples (0.15 to 0.45 ml) were deproteinized (addition of an equal volume of $HClO_4$; 1.6 mol/l), centrifuged and neutralized by addition of $KHCO_3$(6 mol/l). After renewed centrifugation, 0.1 ml of the supernatant was used for the assay in each case.

Enzymatic assay: The enzymatic assay mixture contained, in a final volume of 1.04 ml,
 0.1M potassium phosphate buffer, pH 6.5;
 0.2 mM NADH;
 0.015 units of D-HicDH (in 20 $\mu$l);
 0.1 ml of deproteinized plasma.
Where the KIC concentration was $\leq 0.1$ mmol/l, 0.5 ml of plasma was used and the amount of enzyme was doubled.

The initial reaction rate was determined at 334 nm in an Eppendorf spectrophotometer (temperature maintained at 25½ C.). By use of a calibration plot which had been constructed with known KIC concentrations, it was possible to determine the KIC value for the particular plasma samples. These plasma values were compared with the KIC values obtained by deproteinization, quinoxalinol derivatization, HPLC and fluorescence detection (338 nm interference excitation filter and 425 nm emission filter) on the basis of calibrated values.

FIG. 2 shows the KIC values measured enzymatically and by chromatography in various plasma samples: twenty-four plasma samples were investigated, including eight samples from patients with maple syrup disease. FIG. 2 shows the very good correlation between the two KIC determination methods. No interference from other constituents of the plasma is observable. Thus, HicDH from *Lactobacillus casei* provides an effective means for diagnosing and monitoring maple syrup urine disease, as well as other conditions characterized by higher-than-normal KIC levels.

The essential advantages of an enzymatic method of the present invention are the rapid measurement procedure (2-3 minutes per measurement, with the possibility of determining several samples in parallel), uncomplicated apparatus (simple single-beam photometer, for instance), and the possibility of automating the measurement method (for example, by the use of NAD-dependent enzymes in automatic analyzers, which is state of the art).

It is self-evident that selective KIC determination according to the invention is not confined to analyses of the blood or urine of patients with maple syrup urine disease. To the contrary, it can be used in every instance where an elevated KIC concentration occurs in the biological material, in particular due to metabolic abnormalities, such as in diabetes, cirrhosis of the liver, renal insufficiency, etc.

The simplicity of the determination provided by the present invention offers the opportunity of wider use. In particular, the present invention encompasses standard packs of reagents, as are customary in effecting modern methods of medical analysis, in the particularly expedient of "analysis kits." Such a kit of the present invention would contain a standardized stock of D-HicDH, preferably divisible for the purpose of carrying out several consecutive assays, in addition to appropriate stock amounts of NADH and buffer. For convenience, the kit would also preferably include means for delivering aliquots of the reagents (enzyme, NADH and buffer) to a liquid sample, for analytical purposes.

What is claimed is:

1. A method for the selective determination of α-ketoisocaproate content in a sample, comprising the steps of:
   (A) providing a sample of deproteinized serum or urine from a subject;
   (B) bringing said sample, in the presence of NADH, into contact with a D-α-hydroxyisocaproic dehydrogenase enzyme that selectively catalyzes conversion of α-ketoisocaproate to α-hydroxyisocaproate, said enzyme being obtained from *Lactobacillus casein* subspecies *pseudoplantarum* or *casei* to produce a sample mixture; and then
   (C) measuring said sample for occurrence of said conversion by measuring a decrease in NADH.

2. A method as claimed in claim 1, wherein said sample is deproteinized serum.

3. A method as claimed in claim 4, wherein said enzyme is isolated from a strain of *Lactobacillus casei* subspecies *pseudoplantarum* deposited under accession number DSM 20008.

4. A method as claimed in claim 2, wherein the decrease in NADH is measured spectrometrically.

5. A method as claimed in claim 2, wherein the sample mixture contains a substrate that consumes NAD+ produced when the α-ketoisocaproate is converted to α-hydroxyisocaproate, said substrate generating a detectable species as it consumes NAD+, the decrease in NADH being measured by detecting said species.

6. A method as claimed in claim 5, wherein the decrease in NADH generates a detectable species which is measured colorimetrically.

* * * * *